US012743776B2

(12) United States Patent
Hisadome et al.

(10) Patent No.: US 12,743,776 B2
(45) Date of Patent: Sep. 22, 2026

(54) INFORMATION PROCESSING DEVICE, INFORMATION PROCESSING METHOD, AND COMPUTER-READABLE RECORDING MEDIUM

(71) Applicant: DEEPEYEVISION INC., Tochigi (JP)

(72) Inventors: Yoichiro Hisadome, Tochigi (JP); Yusuke Kondo, Tochigi (JP)

(73) Assignee: DEEPEYEVISION INC., Shimotsuke (JP)

( * ) Notice: Subject to any disclaimer, the term of this patent is extended or adjusted under 35 U.S.C. 154(b) by 420 days.

(21) Appl. No.: 18/565,216

(22) PCT Filed: Aug. 29, 2022

(86) PCT No.: PCT/JP2022/032337
§ 371 (c)(1),
(2) Date: Jul. 25, 2024

(87) PCT Pub. No.: WO2023/032887
PCT Pub. Date: Mar. 9, 2023

(65) Prior Publication Data

US 2024/0296556 A1 Sep. 5, 2024

(30) Foreign Application Priority Data

Aug. 31, 2021 (JP) ................................ 2021-140629

(51) Int. Cl.
*G06T 7/00* (2017.01)
*G06N 3/092* (2023.01)
(Continued)

(52) U.S. Cl.
CPC .......... *G06T 7/0012* (2013.01); *G06N 3/092* (2023.01); *G06V 10/764* (2022.01);
(Continued)

(58) Field of Classification Search
CPC ......... G06T 7/0012; G06T 2207/20081; G06T 2207/20084; G06T 2207/30104;
(Continued)

(56) References Cited

U.S. PATENT DOCUMENTS

2017/0112377 A1* 4/2017 Shiba ........................ G06T 7/60
2018/0084988 A1 3/2018 Chakravorty et al.
(Continued)

FOREIGN PATENT DOCUMENTS

CN 104137145 A * 11/2014 ............... G06T 5/50
GB 2610712 A * 3/2023 ........... G06N 3/0464
(Continued)

OTHER PUBLICATIONS

Patent Cooperation Treaty, International Search Report, Application No. PCT/JP2022/032337, dated Nov. 15, 2022, in 4 pages.
(Continued)

*Primary Examiner* — Jose L Couso
(74) *Attorney, Agent, or Firm* — PROCOPIO, CORY, HARGREAVES & SAVITCH LLP

(57) ABSTRACT

An information processing device, an information processing method, and a computer-readable recording medium that are capable of generating, with a smaller amount of learning data, a learned model that infers a blood circulation anomalous area in a medical image are provided.

A learning unit 124 and a model output unit 126 are provided. The learning unit 124 is configured to cause a machine learning model 125 to learn by inputting medical images and blood vessel images into the machine learning model, the medical images being provided with annotation information of a blood circulation anomalous area, the blood vessel images being obtained by estimating a blood vessel
(Continued)

area in the medical images based on the medical images. The model output unit 126 outputs a learned model having learned at the learning unit.

14 Claims, 6 Drawing Sheets

(51) Int. Cl.

| | |
|---|---|
| ***G06V 10/764*** | (2022.01) |
| ***G06V 10/774*** | (2022.01) |
| ***G06V 10/776*** | (2022.01) |
| ***G06V 10/82*** | (2022.01) |
| ***G16H 30/40*** | (2018.01) |

(52) U.S. Cl.

CPC .......... *G06V 10/774* (2022.01); *G06V 10/776* (2022.01); *G06V 10/82* (2022.01); *G16H 30/40* (2018.01); *G06T 2207/20081* (2013.01); *G06T 2207/20084* (2013.01); *G06T 2207/30104* (2013.01); *G06V 2201/03* (2022.01)

(58) Field of Classification Search

CPC ............. G06T 2207/30041; G06T 5/70; G06T 7/0014; G06T 7/11; G06T 7/97; G06T 2207/10064; G06T 2207/10081; G06T 2207/10101; G06T 2207/10024; G06T 2207/30101; G06T 3/4046; G06T 5/60; G06T 9/002; G06T 2207/20076; G06T 2211/441; G06N 3/092; G06N 3/045; G06N 20/00; G06N 3/02; G06N 3/08–088; G06N 3/04; G06N 3/0445; G06N 3/0454; G06N 3/0464; G06N 3/4046; G06N 3/4053; G06N 3/049; G06N 3/0499; G06N 7/00; G06N 7/01; G06V 10/764; G06V 10/774; G06V 10/776; G06V 10/82; G06V 2201/03; G06V 40/15; G06V 40/18; G06V 10/454; G06V 10/54; G06V 10/7764; G06V 10/84; G06V 20/41; G06V 30/18057; G06V 20/698; G06V 30/19173; G06V 30/194; G16H 30/40; G16H 50/20; G16H 30/20; G16H 50/30; G16H 50/50; G16H 50/70; G16H 10/60; A61B 3/12; A61B 3/14; A61B 3/0025; A61B 5/1128; A61B 3/102; A61B 3/1241; A61B 3/10; A61B 5/02; A61B 5/021; A61B 5/4842; A61B 5/02007; A61B 6/032; A61B 8/0291; G06K 7/1482; G06F 18/213; G06F 18/214; G06F 18/22; G06F 18/241; G06F 18/24; G06F 18/2411; G06F 18/2415; G06F 18/253; G06F 30/27; Y10S 128/925

See application file for complete search history.

(56) References Cited

U.S. PATENT DOCUMENTS

| | | | | |
|---|---|---|---|---|
| 2018/0330518 | A1 | 11/2018 | Choi | |
| 2020/0202527 | A1 | 6/2020 | Choi et al. | |
| 2021/0000343 | A1* | 1/2021 | Kurihara .................. | A61B 3/14 |
| 2021/0158525 | A1* | 5/2021 | Iwase .................. | A61B 3/0025 |

FOREIGN PATENT DOCUMENTS

| | | | |
|---|---|---|---|
| JP | 2019-209136 | A | 12/2019 |
| JP | 2021-086560 | A | 6/2021 |
| KR | 2020-0069209 | A | 6/2020 |
| WO | 2019/142910 | A1 | 7/2019 |
| WO | 2019/246250 | A1 | 12/2019 |

OTHER PUBLICATIONS

Qicheng Lao et al., Leveraging Disease Progression Learning for Medical Image Recognition, arXiv:1806.10128v2, pp. 1-6, Sep. 1, 2018.

* cited by examiner

INFORMATION PROCESSING DEVICE, INFORMATION PROCESSING METHOD, AND COMPUTER-READABLE RECORDING MEDIUM

CROSS-REFERENCE TO RELATED APPLICATIONS

This application is US National Stage of International Patent Application PCT/JP2022/032337, filed Aug. 29, 2022, which claims benefit of priority from Japanese Patent Application 2021-140629, filed Aug. 31, 2021, the contents of both of which are incorporated herein by reference.

TECHNICAL FIELD

The present disclosure relates to an information processing device, an information processing method, and a computer-readable recording medium.

BACKGROUND ART

It is important to understand retinal circulation dynamics for a retinal disease such as diabetic retinopathy that an ischemic condition is caused by blood vessel failure. The retinal circulation dynamics can be understood by performing fluorescein eye-fundus angiography examination. The fluorescein eye-fundus angiography examination can obtain useful information but has a certain amount of load on a patient and a medical worker, such as potential occurrence of an adverse effect due to contrast dye. Thus, a method has been disclosed that specifies a circulation abnormal finding from an eye-fundus image without performing the fluorescein eye-fundus angiography examination.

CITATION LIST

Patent Literature

Patent Literature 1: WO 2019/142910

SUMMARY OF INVENTION

Patent Literature 1 discloses a diagnosis support device configured to specify a blood circulation anomalous area in an eye-fundus image, which is an image of the eye fundus, by using a learned model having learned the relation between an eye-fundus image and a blood circulation anomalous area in the eye-fundus image based on eye-fundus images and blood circulation anomalous areas specified based on fluorescein eye-fundus angiographic images of the eye fundus.

In order to generate such a learned model, it is needed to perform annotation that provides a tag indicating a blood circulation anomalous area, and obtain a large amount of eye-fundus images provided with such information (hereinafter referred to as annotation information). A non-perfusion area (NPA) (hereinafter also referred to as "NPA area") that is an example of a blood circulation anomalous area is an area in which blood does not flow or hardly flows due to, for example, blockage of the retina capillary vascular bed at the eye fundus. An eye-fundus image provided with annotation information of an NPA area is produced as described below. First, a set of an eye-fundus image and a fluorescein eye-fundus angiographic image that are captured for the same patient in the same medical examination is prepared. Subsequently, an ophthalmology specialist or the like annotates an NPA area in the fluorescein eye-fundus angiographic image while observing both images. Lastly, annotation information is provided to the eye-fundus image. As for an area where a neovascularization occurred that is another example of a blood circulation anomalous area, as well, the same process is needed to provide an eye-fundus image with annotation information. Such learning data collection requires a large amount of time and work.

Furthermore, unlike normal semantic segmentation, annotation of an NPA area needs specification of an area having an unclear boundary in a fluorescein eye-fundus angiographic image. This makes learning data collection more difficult.

Thus, it is an object of a first aspect of the present disclosure to provide an information processing device, an information processing method, and a computer-readable recording medium that are capable of generating, with a smaller amount of learning data, a learned model that infers a blood circulation anomalous area in a medical image acquired by image capturing of an examination target site of a patient. It is an object of a second aspect of the present disclosure to provide an information processing device, an information processing method, and a computer-readable recording medium that are capable of highly accurately inferring a blood circulation anomalous area in a medical image as compared to conventional technologies.

An information processing device according to an aspect of the present disclosure includes a learning unit configured to cause a machine learning model to learn by inputting medical images and blood vessel images to the machine learning model, the medical images being provided with annotation information of a blood circulation anomalous area, the blood vessel images being obtained by estimating a blood vessel area in the medical images based on the medical images; and a model output unit configured to output a learned model having learned at the learning unit.

According to this aspect, since the blood vessel images derived from the medical images are used for learning of the machine learning model, the machine learning model can efficiently perform learning as compared to a case in which learning is performed only with the medical images, and as a result, learning can be converged with a smaller amount of learning data.

The above-described information processing device may further include a learning data acquisition unit configured to acquire medical images provided with annotation information so that a ratio of the number of medical images including a blood circulation anomalous area and the number of medical images including no blood circulation anomalous area is equal to a certain ratio. According to this aspect, it is possible to avoid a disadvantageous situation for learning where the number of medical images including no blood circulation anomalous area in learning data is significantly larger than the number of medical images including a blood circulation anomalous area.

In the above-described information processing device, the learning unit may cause the machine learning model to learn by using a loss function that dynamically attenuates a weight of a cross entropy loss of an area that is easy to infer. According to this aspect, it is possible to prevent learning of the machine learning model from being dominated by learning of areas that include no blood circulation anomalous area and are easy to infer, and perform effective learning of areas that include a blood circulation anomalous area and are difficult to infer.

In the above-described information processing device, the blood circulation anomalous area may include a non-perfusion area and an area where a neovascularization occurred, and the learning unit may cause the machine learning model to learn based on at least ordinal scales of a non-anomalous area, a non-perfusion area, and an area where a neovascularization occurred. According to this aspect, it is possible to efficiently cause the machine learning model to learn the order relation of a non-anomalous area, an NPA area, and an area where a neovascularization occurred, and as a result, it is possible to expect convergence of learning with a smaller amount of learning data.

In the above-described information processing device, the learning unit may cause the machine learning model to learn by using a loss function that takes account of an error in classification between areas with the order of a non-anomalous area, a non-perfusion area, and an area where a neovascularization occurred. According to this aspect, it is possible to efficiently cause the machine learning model to learn the order relation of a non-anomalous area, an NPA area, and an area where a neovascularization occurred, and as a result, it is possible to expect convergence of learning with a smaller amount of learning data.

In the above-described information processing device, the learning unit may cause the machine learning model to learn by using, as the annotation information, learning data provided with probability distribution including probabilities allocated to other areas related to ground truth data. According to this aspect, it is possible to efficiently cause the machine learning model to learn the order relation of a non-anomalous area, an NPA area, and an area where a neovascularization occurred, and as a result, it is possible to expect convergence of learning with a smaller amount of learning data.

A method for generating a learned model according to another aspect of the present disclosure comprises acquiring medical images provided with annotation information of a blood circulation anomalous area; acquiring blood vessel images obtained by estimating a blood vessel area in the medical images based on the medical images; causing a machine learning model to learn by inputting the medical images and the blood vessel images to the machine learning model; and outputting a learned model obtained through the learning.

An information processing device according to another aspect of the present disclosure includes a first acquisition unit configured to acquire a first image including a medical image; a second acquisition unit configured to acquire, from the first image, a second image indicating a blood vessel area in the first image; an inference unit configured to infer a blood circulation anomalous area in the first image based on the first image and the second image; and an output unit configured to output a result of the inference by the inference unit.

According to this aspect, since the second image, which is derived from the first image including the inference target medical image and indicates the blood vessel area in the first image, is used to infer the blood circulation anomalous area, it is possible to highly accurately perform the inference as compared to a case in which the inference is performed only with the medical image.

In the above-described information processing device, the second acquisition unit may acquire the second image by inputting the first image to a first learned model, and the first learned model may be a learned model having learned to estimate a blood vessel area based on a medical image. According to this aspect, it is possible to easily acquire the second image having desired accuracy.

In the above-described information processing device, inference unit may infer the blood circulation anomalous area in the first image by inputting the first image and the second image to a second learned model, and the second learned model may be a learned model having learned to estimate a blood circulation anomalous area in a medical image based on the medical image and a blood vessel image that is acquired by inputting the medical image to a first learned model and indicates a blood vessel area in the medical image. According to this aspect, it is possible to obtain an inference result at desired accuracy for the blood circulation anomalous area in the first image.

In the above-described information processing device, the second learned model may be a neural network and may include a convolutional layer with a large stride. According to this aspect, the second learned model can estimate the blood circulation anomalous area in the medical image by using information of the blood vessel area as information of a global range.

The above-described information processing device may further include a classification unit configured to classify the first image into an image that can include a blood circulation anomalous area and other images, and only the image that can include a blood circulation anomalous area may be processed by the inference unit. According to this aspect, it is possible to efficiently perform highly accurate inference.

In the above-described information processing device, the blood circulation anomalous area may include at least one of a non-perfusion area and an area where a neovascularization occurred. According to this aspect, it is possible to perform inference for one or both of the non-perfusion area and the new-blood-vessel generated area in the medical image.

A method according to another aspect of the present disclosure includes acquiring a first image including a medical image; acquiring, from the first image, a second image indicating a blood vessel area in the first image; inferring a blood circulation anomalous area in the first image based on the first image and the second image; and outputting a result of the inference.

A computer-readable recording medium according to another aspect of the present disclosure records a computer program configured to cause one or a plurality of computers to execute acquiring a first image including a medical image; acquiring, from the first image, a second image indicating a blood vessel area in the first image; inferring a blood circulation anomalous area in the first image based on the first image and the second image; and outputting a result of the inference.

Advantageous Effects of Invention

According to a first aspect of the present disclosure, it is possible to provide an information processing device, an information processing method, and a computer-readable recording medium that are capable of generating, with a smaller amount of learning data, a learned model that infers a blood circulation anomalous area in a medical image. According to a second aspect of the present disclosure, it is possible to provide an information processing device, an information processing method, and a computer-readable recording medium that are capable of highly accurately inferring a blood circulation anomalous area in a medical image as compared to conventional technologies.

DESCRIPTION OF EMBODIMENTS

Embodiments of the present invention will be described below with reference to the accompanying drawings. Note that the embodiments described below are intended to facilitate understanding of the present invention and not to limit interpretation of the present invention. The present invention may be modified in various manners without departing from the scope of the present invention. Moreover, the skilled person in the art may employ an embodiment in which elements described below are replaced with their equivalents, and such an embodiment is included in the range of the present invention.

(System Configuration)

Figure 1:
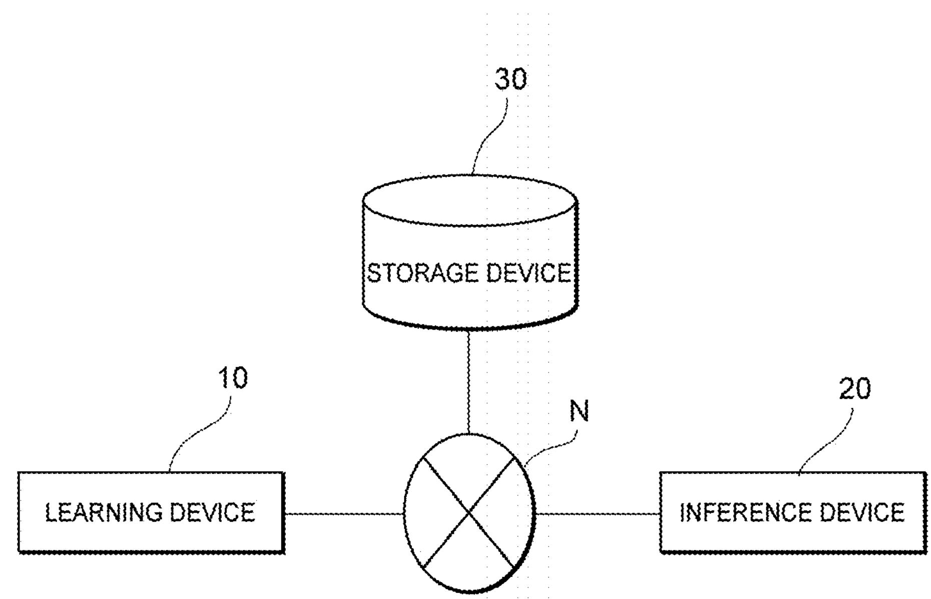
FIG. 1 is a diagram illustrating a network configuration of an information processing system according to an embodiment.
Figure 2:
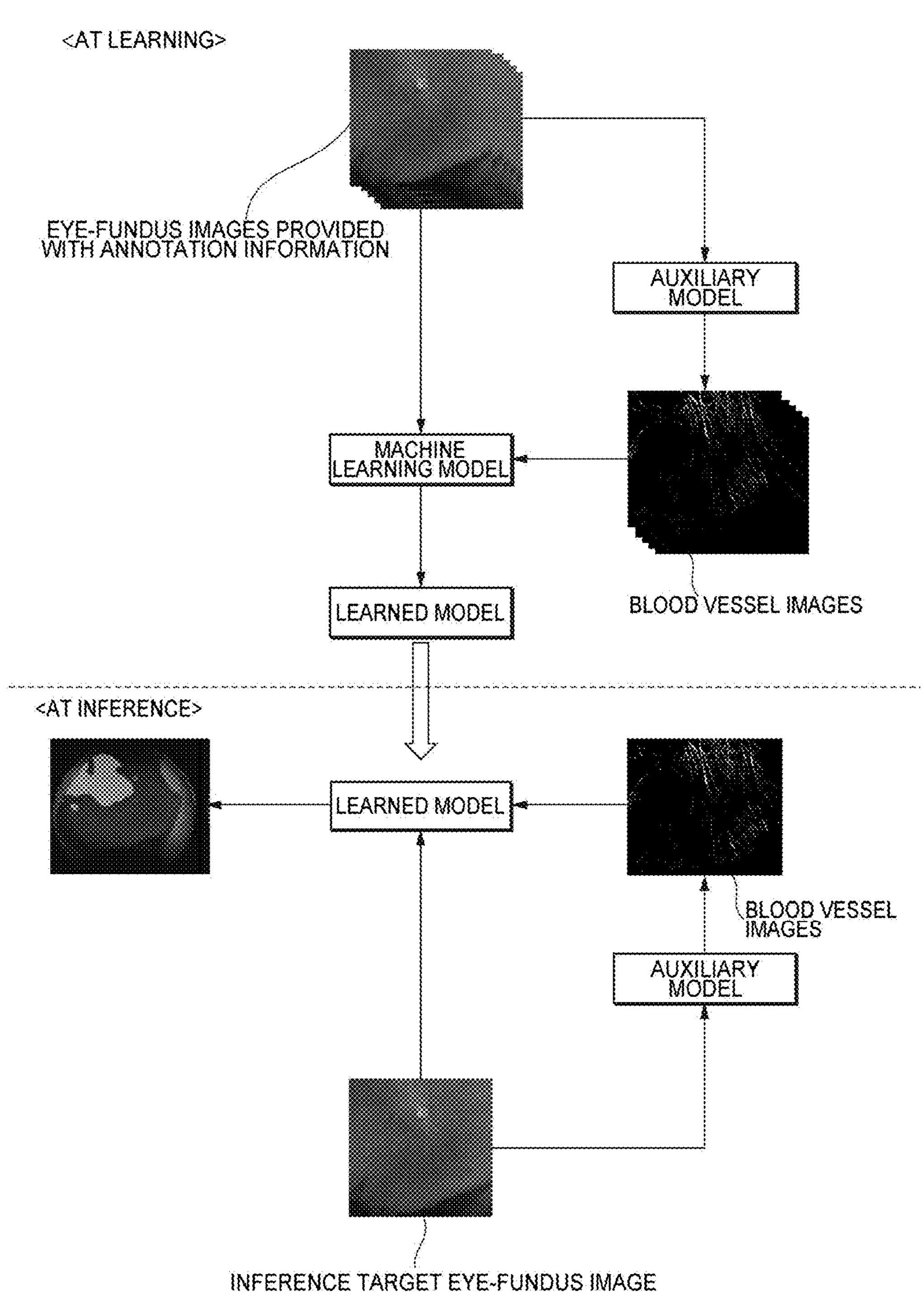
FIG. 2 is a schematic diagram for description of processing by a learning device and processing by an inference device according to an embodiment.

An outline of the present disclosure will be described below with reference to FIGS. 1 and 2. FIG. 1 is a diagram illustrating a network configuration of an information processing system according to an embodiment. FIG. 2 is a schematic diagram for description of processing by a learning device and processing by an inference device according to an embodiment.

An information processing system 1 includes a learning device 10, an inference device 20, and a storage device 30. The learning device 10 is connected to the inference device 20 and the storage device 30 through a communication network N. The communication network N may be any of a wired communication network and a wireless communication network that are constituted by wired and wireless lines and may be the Internet or a local area network (LAN).

The learning device 10 performs learning of a machine learning model based on learning data stored in the storage device 30 and stores a learned model in the storage device 30. The machine learning model is included in the learning device 10 according to the present embodiment, but may be included in a device separated from the learning device 10.

The machine learning model is a model that has a certain model structure and processing parameters varying in accordance with learning processing, and identification accuracy of which improves through optimization of the processing parameters based on experience obtained from learning data. In other words, the machine learning model is a model that learns optimum processing parameters through learning processing. The algorithm of the machine learning model may be, for example, support vector machine, logistic regression, or neural network but is not limited to a particular kind. The machine learning model that performs the learning includes a model that already has performed some learning with learning data, and a model that is yet to perform learning.

Note that a learned model is a model obtained by performing learning of a machine learning model of an optional machine learning algorithm by using appropriate learning data in advance. However, the learned model does not necessarily perform no further learning but may perform additional learning.

The inference device 20 outputs output data in accordance with characteristics of input data by using a learned model. The inference device 20 according to the present embodiment performs inference by using the learned model acquired from the storage device 30. Acquisition of a learned model means acquisition of information necessary for the inference device 20 to reproduce functions of the learned model. For example, in a case in which a neural network is used as the machine learning model, acquisition of a learned model means acquisition of at least the number of layers of the neural network, the number of nodes related to each layer, weight parameters of links connecting nodes, bias parameters related to each node, and information related to the function forms of activation functions related to each node.

The storage device 30 stores learning data to be used for learning of the machine learning model. The storage device 30 according to the present embodiment stores, as the learning data, eye-fundus images provided with annotation information of an NPA area. The storage device 30 also stores learned models output from the learning device 10. The storage device 30 is illustrated as a single storage device in FIG. 1 but may be constituted by one or a plurality of file servers. In the present embodiment, the learning data is eye-fundus images provided with annotation information of an NPA area, which is an example of a blood circulation anomalous area, but in another embodiment, the learning data may be eye-fundus images provided with annotation information of another blood circulation anomalous area such as an area where a neovascularization occurred or the learning data may be eye-fundus images provided with annotation information of both an NPA area and an area where a neovascularization occurred.

As illustrated in FIG. 2, the learning device 10 according to the present embodiment uses an auxiliary model (first learned model) at learning of the machine learning model. The auxiliary model of the present embodiment is a learned model configured to receive, as input data, an eye-fundus image that is learning data for the machine learning model and to output a blood vessel image obtained by estimating a blood vessel area in the eye-fundus image. At learning of the machine learning model, the learning device 10 uses, as input data, a plurality of blood vessel images output from the auxiliary model in addition to a plurality of eye-fundus images provided with annotation information. The present embodiment will be described with an example in which eye-fundus images, which are an example of medical images, are used, but in another embodiment, images acquired by image capturing of another examination target site of a patient, such as brain images or cardiac muscle images may be used.

Since blood vessel images derived from eye-fundus images are used for learning of the machine learning model, the machine learning model can efficiently perform learning as compared to a case in which learning is performed only with eye-fundus images provided with annotation information, and as a result, learning can be converged with a smaller amount of learning data. Learning data for the auxiliary model is images provided with annotation information of a blood vessel area having a clear boundary. Thus, learning data for the auxiliary model can be relatively easily collected.

Similarly, the inference device 20 according to the present embodiment uses the auxiliary model (first learned model) at inference using a learned model (second learned model). As input data to a learned model that infers an NPA area, the inference device 20 uses, in addition to inference target eye-fundus images (first images), blood vessel images (second images) output from the auxiliary model for the eye-fundus images as input data. Since the blood vessel images derived from the eye-fundus images are used for inference of an NPA area, the inference can be highly accurately performed as compared to a case in which the inference is performed only with the eye-fundus images. In the present embodiment, an NPA area is inferred as an example of a blood circulation anomalous area, but in another embodiment, another blood circulation anomalous area such as an area where a neovascularization occurred may be inferred or both an NPA area and an area where a neovascularization occurred may be inferred.

Note that it is difficult to infer an NPA area directly from a learned model that estimates a blood vessel area in an eye-fundus image. This is because, although inference of the position of a blood vessel mainly uses local information, inference of an NPA area needs information of a wider area.

(Functional Configuration: Learning Device)

Figure 3:
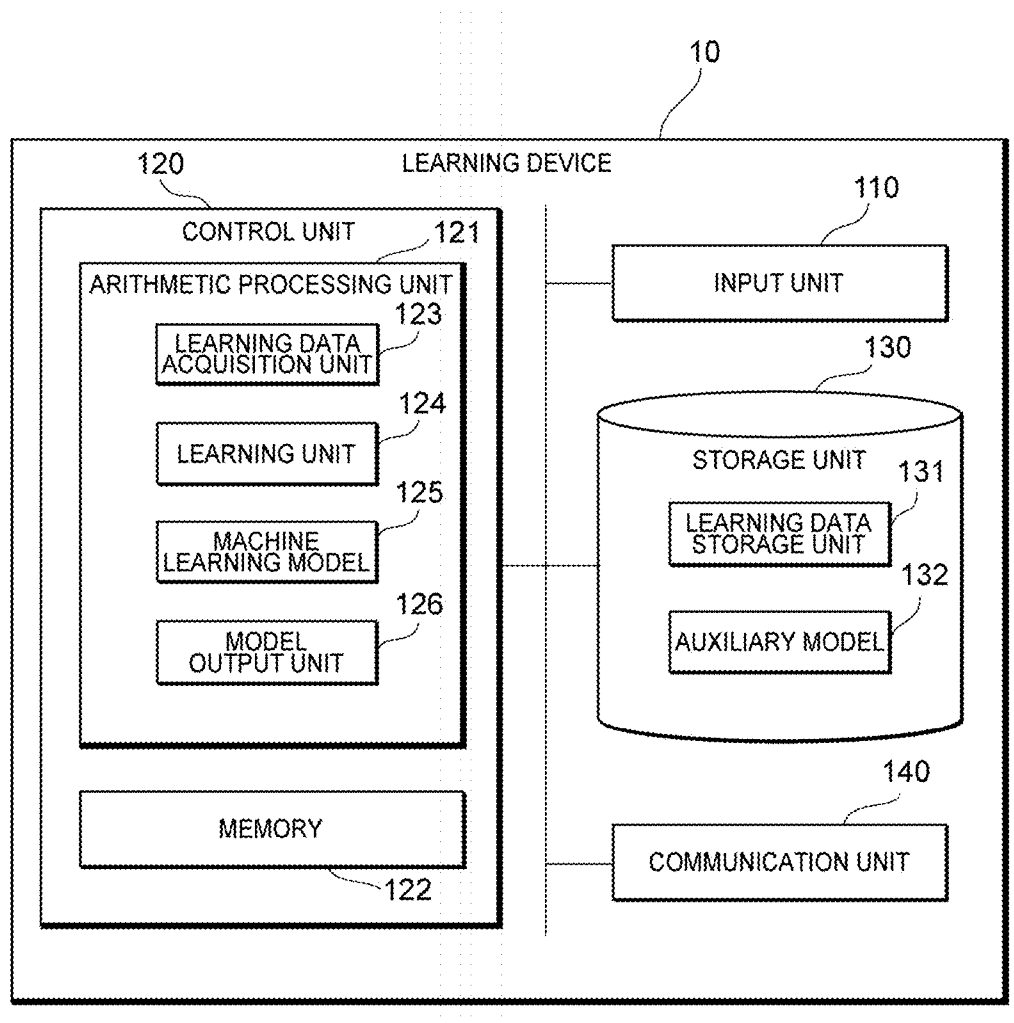
FIG. 3 is a block diagram of the learning device according to an embodiment.

FIG. 3 is a block diagram of the learning device according to an embodiment. Note that, in FIG. 3, a single learning device 10 is assumed and only a necessary functional configuration thereof is illustrated, but the learning device 10 may be configured as part of a multi-function distributed system constituted by a plurality of computer systems.

The learning device 10 includes an input unit 110, a control unit 120, a storage unit 130, and a communication unit 140.

The input unit 110 is configured to receive an operation from an administrator of the learning device 10 and may be achieved by a keyboard, a mouse, a touch panel, or the like.

The control unit 120 includes an arithmetic processing unit 121, such as a CPU or an MPU, corresponding to a processor, and a memory 122 such as a RAM. The arithmetic processing unit (processor) 121 loads, based on various inputs, a computer program recorded in the storage unit 130 onto the memory 122 and executes the computer program, thereby achieving functions and processing at the arithmetic processing unit 121 to be described later. The computer program may be stored in a computer-readable non-transitory recording medium such as a CD-ROM or distributed through a network and may be installed on a computer. The memory 122 functions as a work memory necessary for program execution by the arithmetic processing unit (processor) 121.

The storage unit 130 is configured of a storage device such as a hard disk and records various computer programs necessary for processing execution at the control unit 120, data necessary for execution of various computer programs, and the like. In the present embodiment, the storage unit 130 preferably includes a learning data storage unit 131 and an auxiliary model 132.

The learning data storage unit 131 stores learning data to be used for learning of a machine learning model 125 to be described later. In the present embodiment, the learning data storage unit 131 stores eye-fundus images provided with annotation information of an NPA area.

The auxiliary model 132 stores a learned model used as an auxiliary for learning of the machine learning model 125. In the present embodiment, the auxiliary model 132 stores a learned model that receives an eye-fundus image as input data and outputs a blood vessel image obtained by estimating a blood vessel area in the eye-fundus image. For example, in an embodiment, a learned model having learned by using eye-fundus images provided with annotation information of a blood vessel area may be used as the auxiliary model 132.

The communication unit 140 is configured to connect the learning device 10 to a network. For example, the communication unit 140 may be achieved by a LAN card, an analog modem, or an ISDN modem, and an interface for connecting them to a processing unit through a transmission path such as a system bus.

As illustrated in FIG. 3, the arithmetic processing unit 121 includes, as functional components, a learning data acquisition unit 123, a learning unit 124, the machine learning model 125, and a model output unit 126.

The learning data acquisition unit 123 acquires learning data to be used for learning of the machine learning model 125 to be described later and stores the learning data in the learning data storage unit 131. In the present embodiment, the learning data acquisition unit 123 acquires eye-fundus images provided with annotation information of an NPA area from the storage device 30 and stores the eye-fundus images in the learning data storage unit 131. In an embodiment, the learning data acquisition unit 123 acquires, from the storage device 30, learning data including eye-fundus images including an NPA area and eye-fundus images including no NPA area. The learning data acquisition unit 123 may acquire learning data so that the ratio of the number of eye-fundus images including an NPA area and the number of eye-fundus images including no NPA area is equal to a certain ratio such as 1:1. In this manner, it is possible to avoid a disadvantageous situation for learning where the number of eye-fundus images including no NPA area in learning data is significantly larger than the number of eye-fundus images including an NPA area.

The learning data acquisition unit 123 also acquires, from an eye-fundus image, a blood vessel image indicating a blood vessel area in the eye-fundus image and stores the blood vessel image in the learning data storage unit 131. In the present embodiment, the learning data acquisition unit 123 acquires a blood vessel image by inputting an eye-fundus image to the auxiliary model 132 and stores the blood vessel image in the learning data storage unit 131.

The learning unit 124 causes the machine learning model 125 to learn by using learning data acquired by the learning data acquisition unit 123. In the present embodiment, the learning unit 124 causes the machine learning model 125 to learn by inputting an eye-fundus image and a blood vessel image derived from the eye-fundus image to the machine learning model 125.

The machine learning model 125 receives, as input data, an eye-fundus image provided with annotation information of an NPA area and a blood vessel image derived from the eye-fundus image, and outputs information indicating an NPA area in the eye-fundus image. The present embodiment will be described with an example in which a neural network is used as an example of the machine learning model 125. However, the neural network is merely an example of the machine learning model 125, and the learning device 10 may use another configuration as the machine learning model 125.

In an embodiment, the machine learning model 125 includes a convolutional layer with a large stride as compared to initial settings of the machine learning model 125. In this manner, the machine learning model 125 can learn information of a blood vessel area as information of a global range.

In an embodiment, the learning unit 124 may cause the machine learning model 125 to learn by using a loss function that dynamically attenuates a weight of a cross entropy loss of an area that is easy to infer. In this manner, it is possible to prevent learning of the machine learning model 125 from being dominated by learning of areas that include no NPA area and are easy to infer, and perform effective learning of areas that include an NPA area and are difficult to infer.

In a case in which eye-fundus images provided with annotation information of both an NPA area and an area where a neovascularization occurred are used as learning data, the learning unit 124 may cause the machine learning model to learn based on at least ordinal scales of a non-anomalous area, a non-perfusion area, and an area where a neovascularization occurred. In an embodiment, the learning unit 124 may exploit such a characteristic that an area where a neovascularization occurred is an area generated as a result of progression of an NPA area, and may cause the machine learning model 125 to learn by using a loss function that takes account of an error in classification between areas with the order of a non-anomalous area, an NPA area, and an area where a neovascularization occurred. For example, the learning unit 124 may cause the machine learning model 125 to learn by using, for an eye-fundus image provided with annotation information of an area where a neovascularization occurred, a loss function with which the error in a case in which an NPA area is inferred is smaller than in a case in which a non-anomalous area is inferred. In this manner, it is possible to efficiently cause the machine learning model to learn the order relation of a non-anomalous area, an NPA area, and an area where a neovascularization occurred, and as a result, it is possible to expect convergence of learning with a smaller amount of learning data.

In a case in which eye-fundus images provided with annotation information of both an NPA area and an area where a neovascularization occurred are used as learning data, the learning unit 124 in an embodiment may exploit such a characteristic that an area where a neovascularization occurred is an area generated as a result of progression of an NPA area, and may cause the machine learning model 125 to learn by using learning data provided with annotation information that takes account of the relation between areas with the order of a non-anomalous area, an NPA area, and an area where a neovascularization occurred. For example, the learning unit 124 may cause the machine learning model 125 to learn by using, as learning data provided with annotation information of an area where a neovascularization occurred, learning data provided with, in place of probability distribution with probabilities of 0, 0, and 1 for a non-anomalous area, an NPA area, and an area where a neovascularization occurred as ground truth data, probability distribution including probabilities allocated to other areas related to ground truth data, such as probability distribution with probabilities of 0, 0.1, and 0.9 for a non-anomalous area, an NPA area, and an area where a neovascularization occurred. In this manner, it is possible to efficiently cause the machine learning model to learn the order relation of a non-anomalous area, an NPA area, and an area where a neovascularization occurred, and as a result, it is possible to expect convergence of learning with a smaller amount of learning data.

When learning of the machine learning model 125 is completed, the model output unit 126 outputs a learned model to the storage device 30. Note that, for example, the learning unit 124 may complete the learning after causing the machine learning model 125 to learn by using a predetermined number of pieces of learning data or when the accuracy of the machine learning model 125 satisfies a certain condition.

(Functional Configuration: Inference Device)

Figure 4:
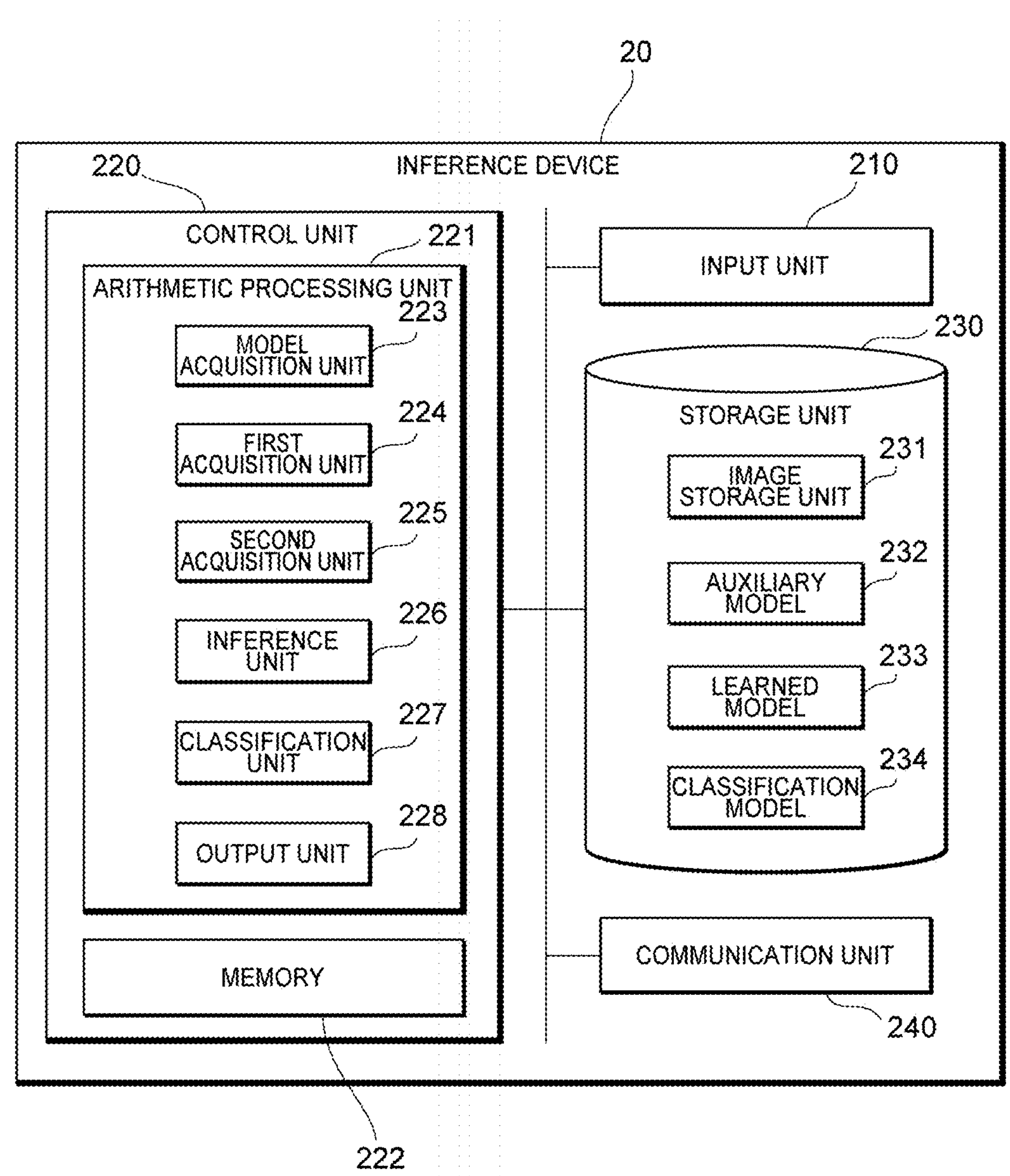
FIG. 4 is a block diagram of the inference device according to an embodiment.

FIG. 4 is a block diagram of an inference device according to an embodiment. Note that, in FIG. 4, a single inference device 20 is assumed and only a necessary functional configuration thereof is illustrated, but the inference device 20 may be configured as part of a multi-function distributed system constituted by a plurality of computer systems.

The inference device 20 includes an input unit 210, a control unit 220, a storage unit 230, and a communication unit 240.

The input unit 210 is configured to receive an operation from an administrator of the inference device 20 and may be achieved by a keyboard, a mouse, a touch panel, or the like.

The control unit 220 includes an arithmetic processing unit 221, such as a CPU or an MPU, corresponding to a processor, and a memory 222 such as a RAM. The arithmetic processing unit (processor) 221 loads, based on various inputs, a computer program recorded in the storage unit 230 onto the memory 222 and executes the computer program, thereby achieving functions and processing at the arithmetic processing unit 221 to be described later. The computer program may be stored in a computer-readable non-transitory recording medium such as a CD-ROM or distributed through a network and may be installed on a computer. The memory 222 functions as a work memory necessary for program execution by the arithmetic processing unit (processor) 221.

The storage unit 230 is configured of a storage device such as a hard disk and records various computer programs necessary for processing execution at the control unit 220, data necessary for execution of various computer programs, and the like. In the present embodiment, the storage unit 230 preferably includes an image storage unit 231, an auxiliary model 232, and a learned model 233. In an embodiment, the storage unit 230 may further include a classification model 234.

The image storage unit 231 stores inference target images. In the present embodiment, the image storage unit 231 stores eye-fundus images in which an NPA area is to be inferred.

The auxiliary model 232 stores a learned model used as an auxiliary for inference. In the present embodiment, the auxiliary model 232 stores a learned model that receives an eye-fundus image as input data and outputs a blood vessel image obtained by estimating a blood vessel area in the eye-fundus image. For example, in an embodiment, a learned model having learned by using eye-fundus images provided with annotation information of a blood vessel area may be used as the auxiliary model 232.

The learned model 233 stores a learned model to be used for inference. In the present embodiment, the learned model 233 stores a learned model configured to receive, as input data, an eye-fundus image and a blood vessel image derived from the eye-fundus image and infer an NPA area in the eye-fundus image. Specifically, the learned model 233 is a learned model having learned by using learning data including an eye-fundus image provided with annotation information of an NPA area and a blood vessel image derived from the eye-fundus image.

The classification model 234 stores a learned model that is used for classification of an input image. In the present embodiment, the classification model 234 stores a learned model configured to receive an eye-fundus image as input data and classify the eye-fundus image into an image that can include an NPA area and other images. Specifically, the classification model 234 is a learned model having learned by using eye-fundus images provided with annotation information indicating whether an NPA area is included. Retinal diseases include a disease with which an NPA area can be generated and a disease unrelated to an NPA area. Learning data for the classification model 234 can be easily collected by exploiting such characteristics of retinal diseases.

The communication unit 240 is configured to connect the inference device 20 to a network. For example, the communication unit 240 may be achieved by a LAN card, an analog modem, or an ISDN modem, and an interface for connecting them to a processing unit through a transmission path such as a system bus.

As illustrated in FIG. 4, the arithmetic processing unit 221 includes, as functional components, a model acquisition unit 223, a first acquisition unit 224, a second acquisition unit 225, an inference unit 226, a classification unit 227, and an output unit 228.

The model acquisition unit 223 acquires a learned model to be used for inference and stores the learned model in the learned model 233. In the present embodiment, the model acquisition unit 223 acquires a learned model from the storage device 30 and stores the learned model in the learned model 233.

The first acquisition unit 224 acquires an inference target image. In the present embodiment, the first acquisition unit 224 acquires, from the image storage unit 231, an eye-fundus image in which an NPA area is to be inferred.

The second acquisition unit 225 acquires a blood vessel image indicating a blood vessel area in the image acquired by the first acquisition unit 224. In the present embodiment, the second acquisition unit 225 inputs an eye-fundus image to the auxiliary model 232 and acquires a blood vessel image indicating a blood vessel area in the eye-fundus image. As described above, the auxiliary model 232 of the present embodiment is a learned model having learned to estimate a blood vessel area from an eye-fundus image.

The inference unit 226 infers an NPA area in an eye-fundus image based on an image acquired by the first acquisition unit 224 and an image acquired by the second acquisition unit 225. In the present embodiment, the inference unit 226 inputs an eye-fundus image acquired by the first acquisition unit 224 and a blood vessel image derived from the eye-fundus image to the learned model 233 and acquires information indicating an NPA area in the eye-fundus image.

In an embodiment, the inference device 20 may use the classification unit 227 as preprocessing of inference. The classification unit 227 classifies an eye-fundus image into an image that can include an NPA area and other images. The classification unit 227 may classify the eye-fundus image by using the classification model 234. When such preprocessing is performed, inference of an NPA area can be performed only for an image that can include an NPA area, and thus it is possible to efficiently perform highly accurate inference.

The output unit 228 outputs an inference result based on information acquired by the inference unit 226. In the present embodiment, the output unit 228 outputs an inference result based on information indicating an NPA area in an eye-fundus image acquired by the inference unit 226. In an embodiment, the output unit 228 may output, in addition to the information indicating an NPA area in the eye-fundus image, the blood vessel image used for the inference.

(Learning Processing)

Figure 5:
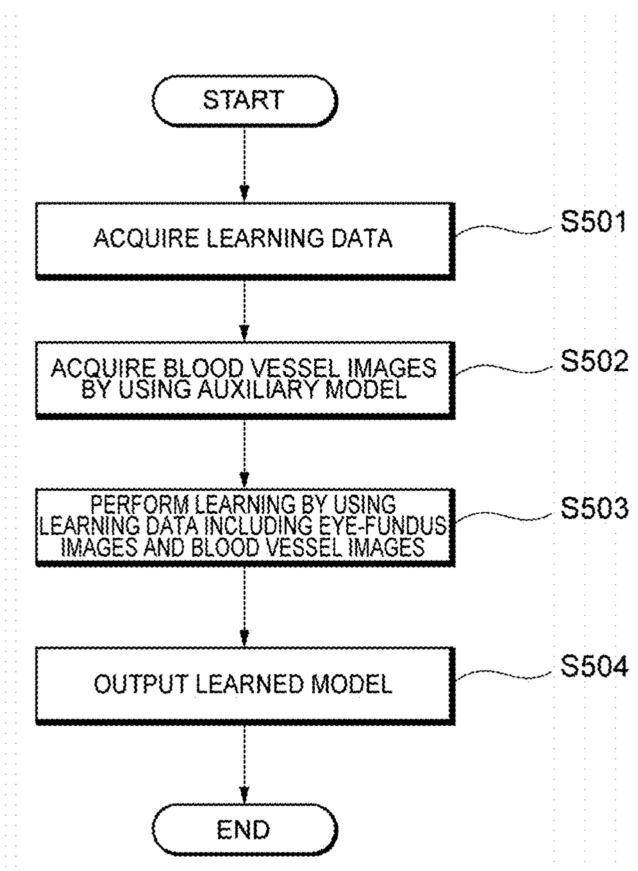
FIG. 5 is a flowchart illustrating learning processing by the learning device according to an embodiment.

Learning processing by the learning device according to an embodiment will be described below in detail with reference to FIG. 5. In the present embodiment, it is assumed that learning data is already stored in the storage device 30 under administration by the administrator of the learning device 10 before the learning processing described with reference to FIG. 5 is performed. Note that the processing illustrated in FIG. 5 is executed, for example, when an instruction for executing processing of generating a learned model is input by the administrator through the input unit 110.

At step S501, the learning data acquisition unit 123 of the learning device 10 acquires learning data to be used for learning of the machine learning model 125 and stores the learning data in the learning data storage unit 131. In the present embodiment, the learning data acquisition unit 123 acquires, from the storage device 30, a plurality of eye-fundus images provided with annotation information of an NPA area and stores the eye-fundus images in the learning data storage unit 131. In this example, the learning data acquisition unit 123 acquires, from the storage device 30, eye-fundus images including an NPA area and eye-fundus images including no NPA area at the ratio of 1:1 in number. In this manner, it is possible to avoid a disadvantageous situation for learning where the number of eye-fundus images including no NPA area in the learning data is significantly larger than the number of eye-fundus images including an NPA area.

Subsequently at step S502, the learning data acquisition unit 123 acquires, from the eye-fundus images, blood vessel images indicating a blood vessel area in the eye-fundus image and stores the blood vessel images in the learning data storage unit 131. In the present embodiment, the learning data acquisition unit 123 acquires blood vessel images by inputting the eye-fundus images to the auxiliary model 132 and stores the blood vessel images in the learning data storage unit 131.

Subsequently at step S503, the learning unit 124 of the learning device 10 causes the machine learning model 125 to learn by using the learning data acquired by the learning data acquisition unit 123. In the present embodiment, the learning unit 124 causes the machine learning model 125 to learn by inputting the eye-fundus images provided with annotation information and the blood vessel images derived from the eye-fundus image to the machine learning model 125.

In the present embodiment, a neural network is used as an example of the machine learning model 125. The machine learning model 125 includes a convolutional layer with a large stride as compared to initial settings of the machine learning model 125 in the present embodiment. In this manner, the machine learning model 125 can learn information of a blood vessel area as information of a global range.

In the present embodiment, the learning unit 124 causes the machine learning model 125 to learn by using a loss function that dynamically attenuates a weight of a cross entropy loss of an area that is easy to infer. In this manner, it is possible to prevent learning of the machine learning model 125 from being dominated by learning of areas that include no NPA area and are easy to infer, and perform effective learning of areas that include an NPA area and are difficult to infer.

At step S504 after the learning of the machine learning model 125 is completed, the model output unit 126 of the learning device 10 outputs the learned model to the storage device 30. Note that, the learning unit 124 may complete the learning, for example, after causing the machine learning model 125 to learn by using a predetermined number of pieces of learning data or when the accuracy of the machine learning model 125 satisfies a certain condition.

(Inference Processing)

Figure 6:
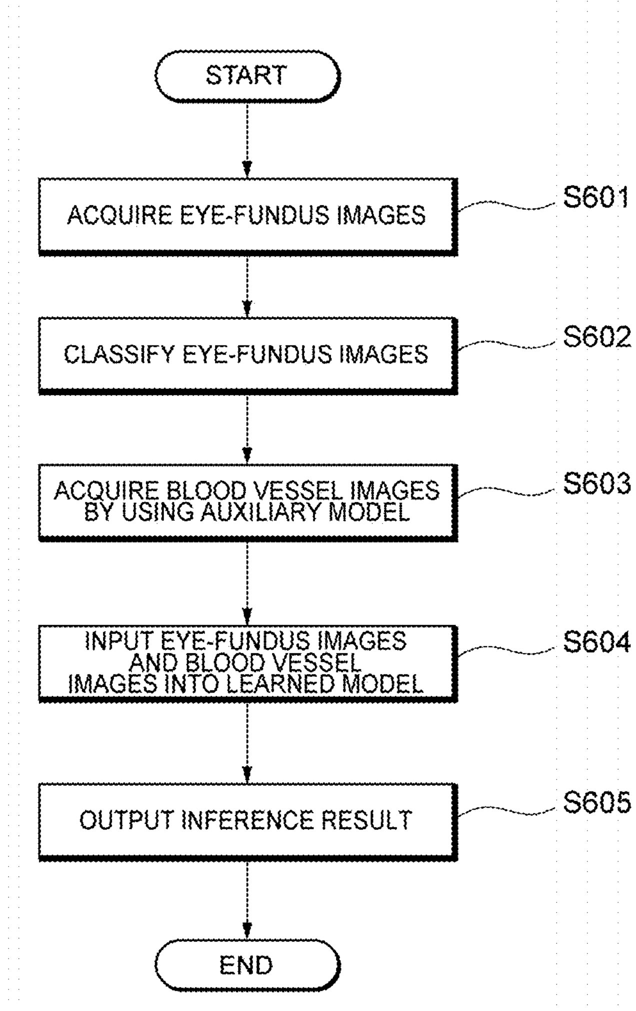
FIG. 6 is a flowchart illustrating inference processing by the inference device according to an embodiment.

Inference processing by the inference device according to an embodiment will be described below in detail with reference to FIG. 6. In the present embodiment, it is assumed that a learned model acquired from the storage device 30 is already stored in the learned model 233 under administration by the administrator of the inference device 20 before the inference processing described with reference to FIG. 6 is performed. It is also assumed that an inference target eye-fundus image is already stored in the image storage unit 231 of the inference device 20. Note that the processing illustrated in FIG. 6 is executed, for example, when an instruction for executing the inference processing is input by the administrator through the input unit 210.

At step S601, the first acquisition unit 224 of the inference device 20 acquires an inference target image. In the present embodiment, the first acquisition unit 224 acquires, from the image storage unit 231, an eye-fundus image in which an NPA area is to be inferred.

At step S602, the classification unit 227 of the inference device 20 classifies the eye-fundus image acquired by the first acquisition unit 224 into an image that can include an NPA area and other images. In this example, the classification unit 227 classifies the eye-fundus image by using the classification model 234. When such preprocessing is performed, inference of an NPA area can be performed only for an image that can include an NPA area, and thus it is possible to efficiently perform highly accurate inference.

At step S603, when an image acquired by the first acquisition unit 224 is an image that can include an NPA area, the second acquisition unit 225 of the inference device 20 acquires a blood vessel image indicating a blood vessel area in the acquired image. In the present embodiment, the second acquisition unit 225 inputs the eye-fundus image acquired by the first acquisition unit 224 to the auxiliary model 232 and acquires a blood vessel image indicating a blood vessel area in the eye-fundus image. As described above, the auxiliary model 232 of the present embodiment is a learned model having learned to estimate a blood vessel area from an eye-fundus image.

At step S604, the inference unit 226 of the inference device 20 infers an NPA area in an eye-fundus image based on an image acquired by the first acquisition unit 224 and an image acquired by the second acquisition unit 225. In the present embodiment, the inference unit 226 inputs the eye-fundus image acquired by the first acquisition unit 224 and the blood vessel image derived from the eye-fundus image to the learned model 233 and acquires information indicating an NPA area in the eye-fundus image.

At step S605, the output unit 228 of the inference device 20 outputs an inference result based on information acquired by the inference unit 226. In the present embodiment, the output unit 228 outputs an inference result as illustrated in FIG. 2 based on the information acquired by the inference unit 226 and indicating an NPA area in the eye-fundus image. In an embodiment, the output unit 228 may output, in addition to the information indicating an NPA area in the eye-fundus image, the blood vessel image used for the inference.

As described above, according to the present embodiment, since the learning device 10 uses, for learning of the machine learning model, blood vessel images derived from eye-fundus images, the machine learning model can be efficiently performed learning as compared to a case in which the learning is performed only with the eye-fundus images, and as a result, learning can be converged with a smaller amount of learning data.

Moreover, according to the present embodiment, since the inference device 20 uses, for inference of an NPA area, a blood vessel image derived from an inference target eye-fundus image, the inference can be highly accurately performed as compared to a case in which the inference is performed only with the eye-fundus image.

REFERENCE SIGNS LIST

10 learning device
110 input unit
120 control unit
121 arithmetic processing unit
122 memory
123 learning data acquisition unit
124 learning unit
125 machine learning model
126 model output unit
130 storage unit
131 learning data storage unit
132 auxiliary model (first learned model)
140 communication unit
20 inference device
210 input unit
220 control unit
221 arithmetic processing unit
222 memory
223 model acquisition unit
224 first acquisition unit
225 second acquisition unit
226 inference unit
227 classification unit
228 output unit
230 storage unit
231 image storage unit
232 auxiliary model (first learned model)
233 learned model (second learned model)
234 classification model
240 communication unit
30 storage device
N communication network

The invention claimed is:

1. An information processing device comprising:
one or more processors; and
a memory storing programs that when executed by the one or more processors cause the one or more processors to:
cause a machine learning model to learn by inputting medical images provided with annotation information of a blood circulation anomalous area to the machine learning model, the blood circulation anomalous area including a non-perfusion area and an area where a neovascularization occurred, the one or more processors being configured to cause the machine learning model to learn based on at least an order relation among a non-anomalous area, a non-perfusion area, and an area where a neovascularization occurred; and
output a learned model obtained through the learning.

2. The information processing device according to claim 1, wherein the programs further cause the one or more processors to acquire medical images provided with annotation information of a blood circulation anomalous area so that a ratio of a number of medical images including a blood circulation anomalous area and the number of medical images including no blood circulation anomalous area is equal to a certain ratio.

3. The information processing device according to claim 1, wherein the one or more processors cause the machine learning model to learn by using a loss function that dynamically attenuates a weight of a cross entropy loss of an area that is easy to infer.

4. A method, performed by one or more processors, for generating a learned model at a system comprising the one or more processors and a memory for storing programs executable by the one or more processors, the method comprising:

acquiring medical images provided with annotation information of a blood circulation anomalous area, the blood circulation anomalous area including a non-perfusion area and an area where a neovascularization occurred;

inputting the medical images to a machine learning model and causing the machine learning model to learn based on at least an order relation among a non-anomalous area, a non-perfusion area, and an area where a neovascularization occurred; and outputting a learned model obtained through the learning.

5. An information processing device comprising:

one or more processors; and a memory storing programs that when executed by the one or more processors cause the one or more processors to:

acquire a first image including a medical image;

infer a blood circulation anomalous area in the first image by inputting the first image to a second learned model, the blood circulation anomalous area including a non-perfusion area and an area where a neovascularization occurred, the second learned model being a learned model having learned to estimate, based on a medical image, a blood circulation anomalous area in the medical image based on at least an order relation among a non-anomalous area, a non-perfusion area, and an area where a neovascularization occurred; and output a result of the inference.

6. The information processing device according to claim 5, wherein the second learned model is a learned model having learned by using medical images provided with annotation information of a blood circulation anomalous area, the medical images being acquired so that a ratio of a number of medical images including a blood circulation anomalous area and the number of medical images including no blood circulation anomalous area is equal to a certain ratio.

7. The information processing device according to claim 5, wherein the programs further cause the one or more processors to acquire a second image indicating a blood vessel area in the first image by inputting the first image to a first learned model, the first learned model being a learned model having learned to estimate a blood vessel area based on a medical image, and wherein the one or more processors infers the blood circulation anomalous area in the first image by inputting the first image and the second image to the second learned model.

8. The information processing device according to claim 5, wherein the second learned model is a neural network and includes a convolutional layer with a large stride.

9. The information processing device according to claim 5, wherein the programs further cause the one or more processors to classify the first image into an image that can include a blood circulation anomalous area and other images, wherein the one or more processors infer a blood circulation anomalous area in the first image by inputting only the image that can include a blood circulation anomalous area to the second learned model.

10. A method, performed by or more processors, at a system comprising the one or more processors and a memory for storing programs executable by the one or more processors, the method comprising:

acquiring a first image including a medical image;

inferring a blood circulation anomalous area in the first image by inputting the first image to a second learned model, the blood circulation anomalous area including a non-perfusion area and an area where a neovascularization occurred, the second learned model being a learned model having learned to estimate, based on a medical image, a blood circulation anomalous area in the medical image based on at least an order relation among a non-anomalous area, a non-perfusion area, and an area where a neovascularization occurred; and outputting a result of the inference.

11. A non-transitory computer-readable recording medium that records a computer program configured to cause one or a plurality of computers to execute:

acquiring a first image including a medical image;

inferring a blood circulation anomalous area in the first image by inputting the first image to a second learned model, the blood circulation anomalous area including a non-perfusion area and an area where a neovascularization occurred, the second learned model being a learned model having learned to estimate, based on a medical image, a blood circulation anomalous area in the medical image based on at least an order relation among a non-anomalous area, a non-perfusion area, and an area where a neovascularization occurred; and outputting a result of the inference.

12. The information processing device according to claim 1, wherein the one or more processors cause the machine learning model to learn by inputting blood vessel images together with the medical images to the machine learning model, the blood vessel images being obtained by estimating a blood vessel area in the medical images based on the medical images.

13. The information processing device according to claim 1, wherein the one or more processors cause the machine learning model to learn by using a loss function that takes account of an error in classification between areas with the order of a non-anomalous area, a non-perfusion area, and an area where a neovascularization occurred.

14. The information processing device according to claim 1, wherein the one or more processors cause the machine learning model to learn by using, as the annotation information, learning data provided with probability distribution including probabilities allocated to other areas related to ground truth data.

* * * * *